(12) United States Patent
Wood et al.

(10) Patent No.: US 7,787,927 B2
(45) Date of Patent: Aug. 31, 2010

(54) SYSTEM AND METHOD FOR ADAPTIVE MEDICAL IMAGE REGISTRATION

(75) Inventors: Chris H. Wood, North Bend, WA (US); Tanya L. Niemeyer, Seattle, WA (US)

(73) Assignee: Merge CAD Inc., Bellevue, WA (US)

( * ) Notice: Subject to any disclaimer, the term of this patent is extended or adjusted under 35 U.S.C. 154(b) by 978 days.

(21) Appl. No.: 10/600,044

(22) Filed: Jun. 20, 2003

(65) Prior Publication Data

US 2004/0260170 A1 Dec. 23, 2004

(51) Int. Cl.
*A61B 5/05* (2006.01)
(52) U.S. Cl. .................... 600/407; 600/410; 600/408; 600/429; 382/128; 378/20; 378/21
(58) Field of Classification Search ............ 382/128, 382/131, 154, 294, 275; 600/42, 407, 408, 600/410, 429, 440–449, 458, 455, 595; 378/20, 378/21
See application file for complete search history.

(56) References Cited

U.S. PATENT DOCUMENTS

| | | | | |
|---|---|---|---|---|
| 6,097,854 | A * | 8/2000 | Szeliski et al. | 382/284 |
| 6,154,518 | A * | 11/2000 | Gupta | 378/62 |
| 6,181,832 | B1 * | 1/2001 | Maas, III | 382/294 |
| 6,266,453 | B1 * | 7/2001 | Hibbard et al. | 382/294 |
| 6,445,182 | B1 * | 9/2002 | Dean et al. | 324/309 |
| 6,464,643 | B1 * | 10/2002 | Brock-Fisher | 600/458 |
| 6,567,533 | B1 * | 5/2003 | Rhoads | 382/100 |
| 6,775,392 | B1 * | 8/2004 | Rhoads | 382/100 |
| 6,965,691 | B2 * | 11/2005 | Walmsley et al. | 382/162 |
| 2003/0088177 | A1 | 5/2003 | Totterman et al. | |
| 2005/0257748 | A1 * | 11/2005 | Kriesel et al. | 119/51.02 |
| 2006/0034545 | A1 * | 2/2006 | Mattes et al. | 382/294 |

OTHER PUBLICATIONS

A Pyramid Approach to Subpixel Registration, Thevenaz et al. Jan. 1999, IEEE Transactions on Image Processing, vol. 7 Is 1.*
Medical Image Registration (Review Article), Hill et al. Jun. 2000, Physics in Medicine and Biology, (46) 2001, R1-R46.*
Philippe Thevenaz et al., "A Pyramid Approach to Subpixel Registration Based on Intensity," IEEE Transactions on Image Processing, Jan. 1998, pp. 27-41, vol. 7, No. 1.
Derek L G Hill et al., "Medical image registration," Physics in Medicine and Biology, Mar. 2001, pp. 1-45, vol. 46, No. 3, IOP Publishing Ltd., UK.

* cited by examiner

*Primary Examiner*—Brian Casler
*Assistant Examiner*—Joel M Lamprecht
(74) *Attorney, Agent, or Firm*—Michael Best & Friedrich LLP

(57) ABSTRACT

In one embodiment, an adaptive medical image registration procedure includes a motion estimation procedure involving estimating or determining an amount of patient or tissue motion along a set of axes; an evaluation procedure involving evaluating an estimated amount of motion relative to a correction threshold; and a correction procedure involving performing a two dimensional image resampling, a three dimensional image resampling, or possibly avoiding an image resampling based upon a relationship between an estimated amount of motion and the correction threshold. Axes considered by a motion estimation procedure may include an axis of lowest image resolution, and the correction threshold may have a value given by a fraction of a lowest image resolution.

50 Claims, 9 Drawing Sheets

SYSTEM AND METHOD FOR ADAPTIVE
MEDICAL IMAGE REGISTRATION

TECHNICAL FIELD

The present disclosure relates generally to medical imaging techniques. More particularly, the present disclosure describes systems and methods for adaptively registering medical images in accordance with relationships between particular parameters, for example, patient movement and spatial resolution.

BACKGROUND

Medical imaging technologies can provide detailed information useful for differentiating, diagnosing, or monitoring the condition, structure, and/or extent of various types of tissue within a patient's body. In general, medical imaging technologies detect and record manners in which tissues respond in the presence of applied signals and/or injected or ingested substances, and generate visual representations indicative of such responses.

A variety of medical imaging technologies exist, including Computed Tomography (CT), Positron Emission Tomography (PET), Single Photon Emission Computed Tomography (SPECT), and Magnetic Resonance Imaging (MRI). Any given medical imaging technology may be particularly well suited for differentiating between specific types of tissues. A contrast agent administered to the patient may selectively enhance or affect the imaging properties of particular tissue types to facilitate improved tissue differentiation. For example, MRI may excel at distinguishing between various types of soft tissue, such as malignant and/or benign breast tumors or lesions that are contrast enhanced relative to healthy breast tissue in the presence of Gadolinium DPTA or another contrast agent.

Particular imaging techniques, for example, certain MRI techniques, may scan a volume of tissue within an anatomical region of interest. Scan data corresponding to an anatomical volume under consideration may be transformed into or reconstructed as a series of planar images or image "slices." For example, data generated during a breast MRI scan may be reconstructed as a set of 40 or more individual image slices. Any given image slice comprises an array of volume elements or voxels, where each voxel corresponds to an imaging signal intensity within an incremental volume that may be defined in accordance with x, y, and z axes or dimensions. The z axis commonly corresponds to a distance increment between image slices, that is, image slice thickness.

Medical imaging techniques may generate or obtain imaging data corresponding to a given anatomical region at different times or sequentially through time to facilitate detection of changes within the anatomical region from one scan series to another. Temporally varying, tissue dependent contrast agent uptake properties may facilitate accurate identification of particular tissue types. For example, in breast tissue, healthy or normal tissue exhibits different contrast agent uptake behavior over time than tumorous tissue. Moreover, malignant lesions exhibit different contrast agent uptake behavior than benign lesions ("Measurement and visualization of physiological parameters in contrast-enhanced breast magnetic resonance imaging," Paul A. Armitage et al., *Medical Imaging Understanding and Analysis*, July 2001, University of Birmingham).

In view of the foregoing, comparisons between 1) an image obtained prior to contrast agent administration (i.e., a "precontrast image") and one or more corresponding images obtained following contrast agent administration (i.e., "postcontrast images"); and/or 2) a temporal sequence of postcontrast images relative to each other may serve to highlight differences between and/or within tissues, thereby aiding medical diagnostic procedures.

Medical images can be characterized by their spatial resolution. As previously indicated, an MRI slice comprises a set of volume elements or voxels, where each voxel corresponds to a signal intensity or value for a quantized tissue volume. An exemplary MRI slice may have a resolution of 256×256 voxels with respect to x and y reference directions or axes, where each voxel represents imaging data for a 1.0×1.0×2.5 mm$^3$ tissue volume relative to x, y, and z axes, respectively.

Successful detection, characterization, and/or identification of tissue boundaries and/or small tissue structures such as newly or recently developed lesions or tissue abnormalities requires the ability to identify tissue boundaries and/or indicate temporal tissue changes at the level of fractional voxels, individual voxels, and/or very small voxel groups. If a patient moves even slightly during or between image acquisition procedures, the imaged shape, size, and/or relative location of a given tissue boundary or structure may be distorted or shifted relative to its actual shape, size, and/or location. Unfortunately, some patient movement will essentially always exist. Patient movement may arise from several sources, including changes in patient relaxation or tension levels over time, for example, prior to, during, and following injection of a contrast agent; minor positional adjustments; and respiration. Patient movement can be particularly problematic when imaging nonrigid or readily deformable anatomical structures such as breasts.

To reduce the effects of patient motion upon imaging accuracy, medical imaging techniques may include registration correction procedures. Current registration correction procedures involve selection of a reference image from within an image series; generation or determination of motion estimation parameters; and motion correction of acquired images with respect to the reference image. The motion correction involves image resampling with subvoxel accuracy. Such resampling may occur, for example, through an interpolation procedure. Unfortunately, image resampling itself can degrade or deteriorate the spatial resolution of imaging information. Such degradation can be dependent upon one or more aspects of the registration correction procedure itself. A need exists for a system and method that situationally consider the potential impact that registration correction may have upon imaging accuracy.

DETAILED DESCRIPTION

The present disclosure describes systems and/or methods for adaptive registration of medical images. Depending upon embodiment details, adaptive medical image registration may be based upon relationships between various imaging parameters and/or results obtained from image analysis. Such parameters and/or results may include image resolution in one or more dimensions; an amount of patient or tissue movement in one or more dimensions; and/or relative imaging signal intensity levels at one or more times for particular categories of tissue. Portions of the following description detail manners in which various embodiments of the present invention may be applied in an MRI context, particularly MRI imaging of breast tissue. Notwithstanding, various embodiments of systems and/or methods in accordance with the present invention may be applicable to essentially any type of medical imaging technology and/or technique that utilizes a contrast agent.

In general, at any particular time, the intensity of an imaging signal associated with any given voxel depends upon the types of tissues within an anatomical region corresponding to the voxel; the presence or absence of a contrast agent in such tissues; and the temporal manners in which such tissues respond following contrast agent administration. In several types of breast MRI situations, normal or healthy tissue exhibits a background signal intensity in the absence of a contrast agent, while abnormal or tumorous tissue exhibits a low or reduced signal intensity relative to the background intensity. Prior to contrast agent administration, abnormal tissue therefore typically appears darker than normal tissue. In the presence of a contrast agent, lesions or certain types of abnormal tissue typically exhibit an enhanced or increased signal intensity relative to the background intensity. In certain breast MRI situations, MRI situations involving other anatomical regions, and/or imaging applications involving other imaging technologies, relationships between background, precontrast, and/or postcontrast signal intensity may differ, in manners understood by those skilled in the art.

On an individual voxel basis, the relative degree to which an imaging signal corresponding to a lesion or abnormal or undesirable tissue is enhanced at any given time following contrast agent administration may be defined as a signal enhancement percentage that is normalized to a lowest signal intensity within a voxel. Commonly, this lowest signal intensity is either the background signal intensity or the abnormal tissue's precontrast signal intensity.

Patient or tissue movement or motion may cause an imaging signal corresponding to a lesion within any particular voxel to be displaced and/or distorted into a set of adjacent, adjoining, and/or proximate voxels in any given direction or dimension. When tissue movement occurs during acquisition of a given single slice, imaging signal distortion affects voxels within the plane of that slice. When tissue movement continues or occurs between one slice acquisition and another, imaging signal displacement and/or distortion can affect voxels in different slices. Following tissue motion, the extent to which a lesion is imaged in an adjacent, adjoining, or proximate voxel relative to voxel resolution may affect signal enhancement percentages for the voxels involved, as further detailed hereafter.

Figure 1:
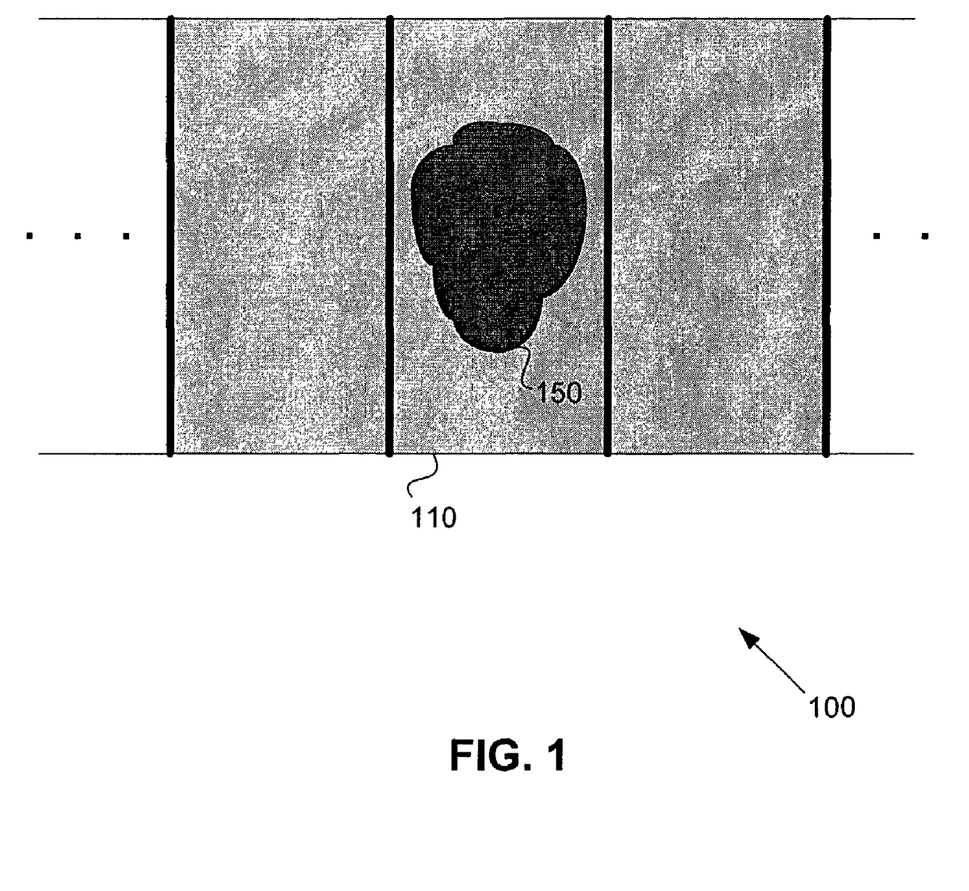
FIG. 1 is a side view schematic illustration of an exemplary precontrast image slice in which a lesion has been imaged within spatial boundaries corresponding to a first voxel.

FIG. 1 is a schematic illustration of an exemplary precontrast image slice 100 in which a lesion 150 has been imaged within spatial boundaries corresponding to a first precontrast voxel 110. In the precontrast slice 100, the lesion 150 may be imaged as having a precontrast signal intensity (shown in dark gray) that is less or lower than a background signal intensity (shown in light gray). Following data or signal corresponding to acquisition of a set or series of precontrast image slices that includes the exemplary precontrast slice 100, a contrast agent may be administered. After contrast agent administration, image acquisition corresponding to a set or series of postcontrast slices may occur. Relative to breast MRI, contrast agent uptake within a lesion may provide a peak postcontrast imaging signal intensity approximately 60 to 90 seconds after contrast agent administration. Patient movement during or after precontrast imaging may affect how the lesion 150 is imaged in one or more postcontrast slices.

Figure 2:
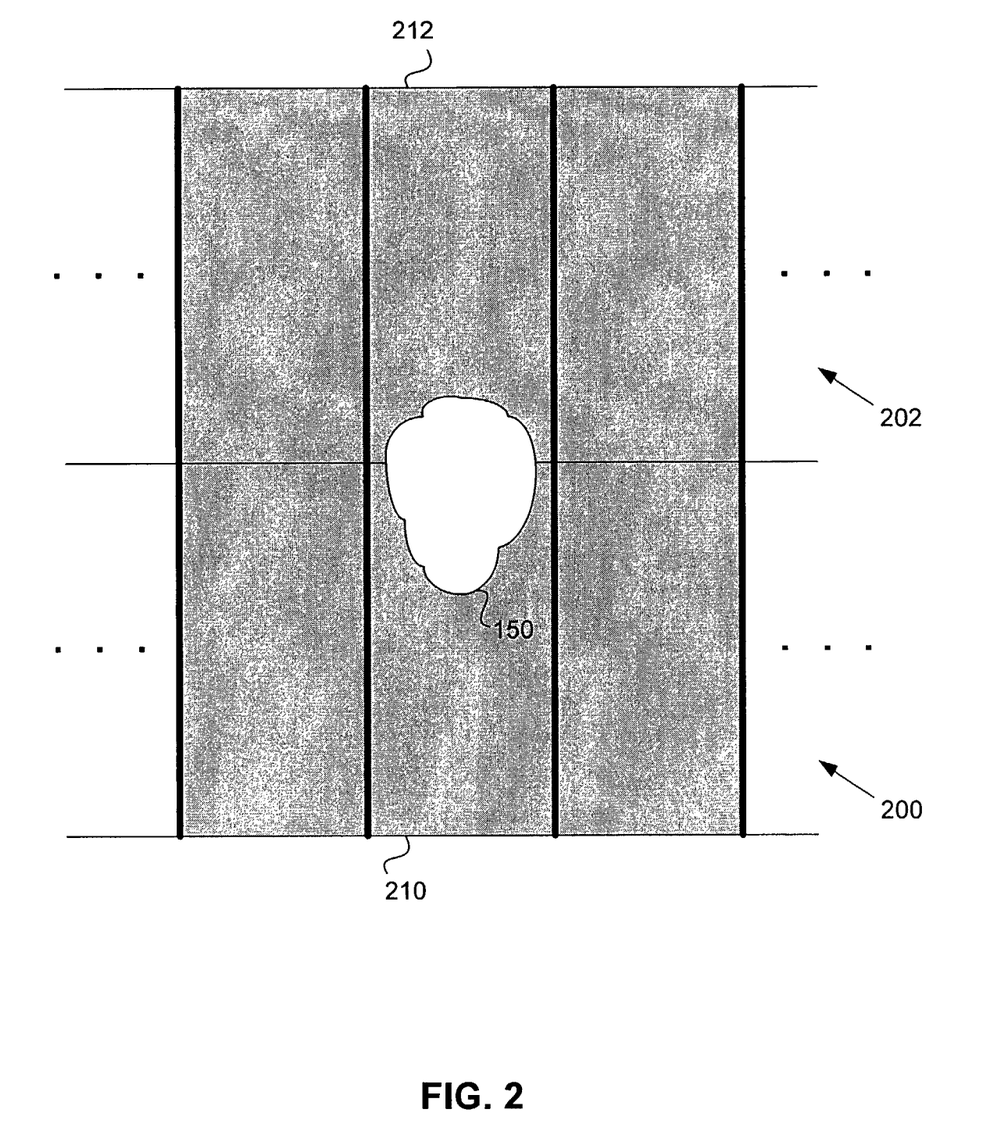
FIG. 2 is a side view schematic illustration of a first and a second exemplary postcontrast image slice in which a lesion has been imaged across a voxel belonging to the first postcontrast slice and a voxel belonging to the second postcontrast slice as a result of patient or tissue motion.

FIG. 2 is a schematic illustration of a first 200 and a second 202 exemplary postcontrast image slice, in which the lesion 150 of FIG. 1 has been imaged as spanning a portion of a first postcontrast voxel 210 within the first postcontrast slice 200 and a portion of a second postcontrast voxel 212 within the second postcontrast slice 202 as a result of patient or tissue motion. In the postcontrast slices 200, 202, the lesion 150 may be imaged as having a postcontrast intensity (shown in white) that is greater or higher than its precontrast intensity.

As a result of patient or tissue motion, the lesion 150 has been imaged within spatial locations corresponding to two voxels 210, 212 across separate slices 200, 202 rather than within a spatial extent corresponding to a single voxel 110 within a single slice 100. Such motion has therefore caused a partial volume artifact or imaging error. In response to this or a similar type of volume artifact or imaging error, the present invention in one embodiment may initiate or perform a registration correction procedure in a selective or adaptive manner.

In the absence of any type of registration correction, an uncorrected signal enhancement percentage corresponding to the first postcontrast voxel 210 may be given by $$\% E_{210\,u} = ((1-\alpha)*POST + \alpha*BG) - PRE)/PRE \quad [1]$$

where BG corresponds to a background signal intensity; PRE corresponds to a precontrast signal intensity associated with the lesion 150; POST corresponds to a postcontrast signal intensity associated with the lesion 150; and $\alpha$ may be defined as a distance that the tissue of interest (i.e., the contrast enhanced lesion) or an imaging signal corresponding thereto has shifted along a particular axis or direction relative to a voxel resolution along that axis or direction. In other words, $\alpha$ may represent a resolution normalized fractional shift of contrast enhanced tissue, which corresponds to a resolution normalized amount of patient motion. The value of $\alpha$ may be a measured, estimated, approximated, and/or derived quantity based upon imaging information and/or implementation details.

In a manner analogous to that for Equation [1], an uncorrected signal enhancement percentage for the second postcontrast voxel 212 may be given by $$\% E_{212\,u} = ((\alpha * POST + (1-\alpha) * BG) - BG)/BG \quad [2]$$

During or in association with registration correction, image resampling may be performed in a variety of manners depending upon implementation details. For example, image resampling may be performed in accordance with a linear, a polynomial, a spline, or a sinc based procedure, or in accordance with essentially any type of resampling technique capable of providing subvoxel accuracy. These registration processes are well know in the art and need not be described in greater detail herein.

In accordance with an exemplary linear interpolation based registration correction, a registration corrected signal enhancement percentage for the first postcontrast voxel 210 may be given by $$\% E_{210c} = \frac{((1-\alpha) * POST + \alpha * BG) - ((1-\alpha) * PRE + \alpha * BG)}{((1-\alpha) * PRE + \alpha * BG)} \quad [3]$$

In like manner, a registration corrected signal enhancement percentage for the second postcontrast voxel 212 may be given by $$\% E_{212c} = \frac{(\alpha * POST + (1-\alpha) * BG) - (\alpha * PRE + (1-\alpha) * BG)}{(\alpha * PRE + (1-\alpha) * BG)} \quad [4]$$

Valuation of Equations [1] through [4] yields different results depending upon the value of $\alpha$. Thus, the degree to which tissue is contrast enhanced depends upon patient motion relative to voxel or image resolution. Furthermore, the numerical behavior of Equations [1] through [4] depends upon relative relationships between background, precontrast, and postcontrast imaging signal intensities. A variety of useful imaging signal intensity reference relationships may be defined, including (a) precontrast signal intensity less than background signal intensity; (b) equal or essentially equal background and precontrast signal intensities; and (c) precontrast signal intensity greater than background signal intensity. In many or most types of breast MR imaging situations, precontrast signal intensity is typically less than background signal intensity and thus reference relationship (a) generally holds. The applicability of a particular signal intensity reference relationship to a given medical imaging situation may depend upon imaging technology and/or techniques employed; tissue types under consideration; contrast agent type; and/or other factors. Manners in which various imaging signal intensity reference relationships may affect an imaging signal enhancement percentage are considered in detail hereafter.

In imaging situations in which an imaging signal intensity or value associated with a postcontrast lesion is expected to be higher or greater than an intensity associated with a precontrast lesion, accurate lesion identification may be aided when a signal enhancement percentage is increased or maximized. Such imaging situations typically include breast MRI. In certain embodiments, the present invention may adaptively select, initiate, and/or perform a registration correction procedure in a manner that maximizes a likelihood of lesion enhancement.

Figure 3:
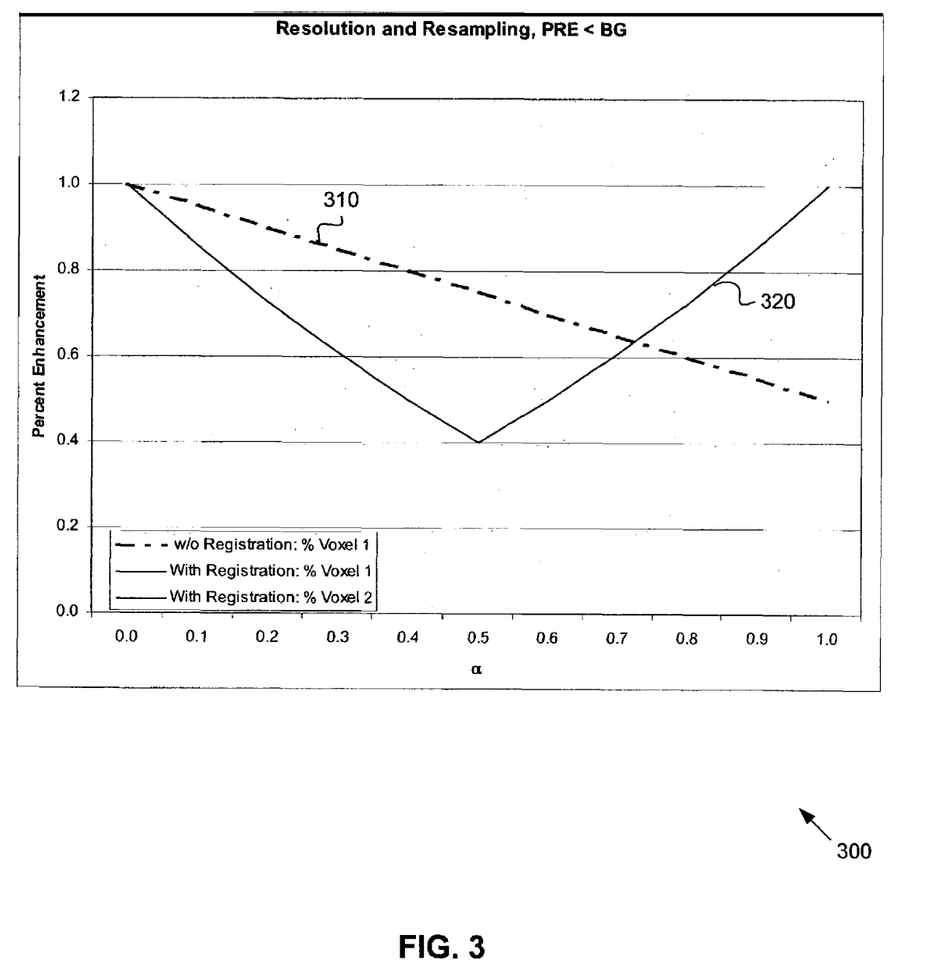
FIG. 3 is a graph relating a fractional normalized tissue displacement to an uncorrected and a corrected postcontrast signal enhancement percentage when precontrast imaging signals are less than or generally less than background imaging signals.

FIG. 3 is a graph 300 relating a fractional normalized tissue displacement $\alpha$ to an uncorrected postcontrast signal enhancement percentage curve or line 310 and a corrected postcontrast signal enhancement percentage curve or line 320 when precontrast imaging signals corresponding to a lesion are less than or generally less than background imaging signals. The curve 320 comprises two curve portions showing the percent enhancement from voxel 1 and voxel 2, respectively, with the curve 320 showing only the maximum value of the percent enhancement. The percent enhancement from voxel 1 is shown on the left portion of the curve 320 for values of $\alpha$ less than approximately 0.5. For values of $\alpha$ greater than 0.5, the portion of the curve 320 is due to the percent enhancement. The uncorrected curve 310 is generated based upon Equation [1], while the corrected curve 320 is based upon Equations [3] and [4]. In FIG. 3, the values of BG, PRE, and POST are respectively defined as 150, 100, and 200.

In FIG. 3, if $\alpha$ is approximately equal to 0.3, for example, a postcontrast enhancement percentage corresponding to the uncorrected curve 310 is higher or larger than that corresponding to the corrected curve 320. In such an imaging situation, one embodiment of the present invention may avoid or omit performing a correction or image resampling in order to enhance or maximize imaging accuracy, such that an imaging result more closely represents or indicates actual lesion boundaries and/or processes occurring therein. In the event that a is approximately equal to 0.8, for example, a corrected curve 320 provides a higher or larger postcontrast enhancement percentage than an uncorrected curve 310, and thus in one embodiment the present invention may perform a correction or image resampling in order to increase, enhance, or maximize imaging accuracy in such a situation.

More generally, below a transition value or a transition range of $\alpha$, an uncorrected curve 310 may provide a higher or larger enhancement percentage than a corrected curve 320, while the corrected curve 320 may provide a higher enhancement percentage than the uncorrected curve 310 above the transition value or transition range of $\alpha$. As shown in FIG. 3, a transition value or transition range of $\alpha$ may be approximately between 0.6 and 0.8. The transition value or transition range of $\alpha$ may vary depending upon imaging technology, clinical conditions, and/or various embodiment details (possibly including a manner of estimating or determining $\alpha$). In imaging situations in which maximization of sensitivity to postcontrast signal enhancement percentage is desired and PRE is expected to be less than BG, particular embodiments of the present invention may initiate or perform a first type of correction, for example, a 2D correction, when a measured, estimated, approximated, or derived value of a is below a certain transition value or falls within a first range; and initiate or perform a second type of correction, for example, a 3D correction, when a value of $\alpha$ is above such a transition value or falls within a second range.

Figure 4:
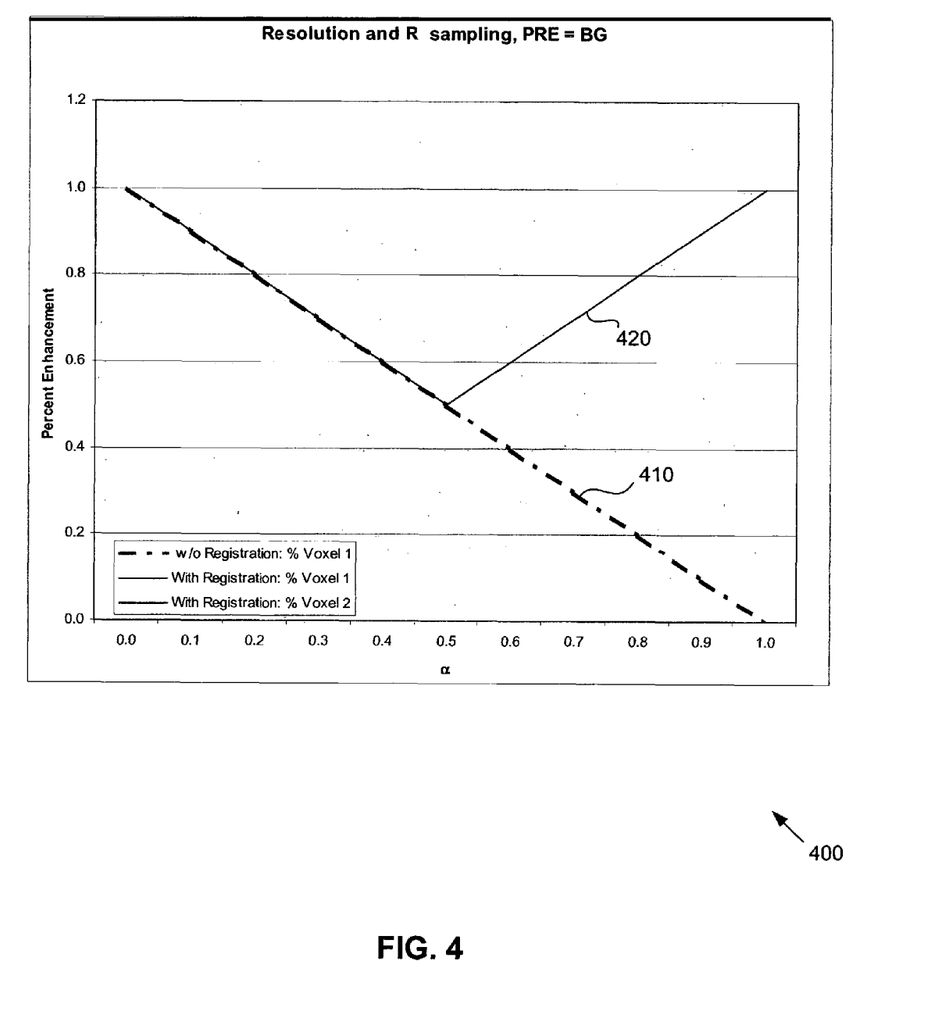
FIG. 4 is a graph relating a fractional normalized tissue displacement to an uncorrected and a corrected postcontrast signal enhancement percentage when precontrast and background imaging signals are equal or essentially equal.

FIG. 4 is a graph 400 relating a fractional normalized tissue displacement $\alpha$ to an uncorrected postcontrast signal enhancement percentage curve or line 410 and a corrected postcontrast signal enhancement percentage curve or line 420 when precontrast and background imaging signals are equal or essentially equal. The curve 420 comprises two curve portions showing the percent enhancement from voxel 1 and voxel 2, respectively, with the curve 420 showing only the maximum value of the percent enhancement. In FIG. 4, the values of BG and PRE are defined as 100, and the value of POST is defined as 200. In a manner similar to that described above with reference to FIG. 3, a transition value for $\alpha$ may approximately equal 0.5, and/or a transition range for $\alpha$ may approximately be between 0.45 and 0.55, under conditions corresponding or generally corresponding to FIG. 4. Thus, imaging accuracy may be enhanced or maximized in certain embodiments by performing a first type of correction or avoiding a correction when $\alpha$ is less than approximately 0.5; and performing a second type of correction when $\alpha$ is greater than approximately 0.5. As indicated in FIG. 4, a correction may be unnecessary, avoided, or omitted when $\alpha$ is less than approximately 0.5 because imaging accuracy is unaffected or generally unaffected in such a situation. That is, the equations defining the uncorrected postcontrast curve 410 and the corrected postcontrast curve 420 generate identical or essentially identical results when $\alpha$ is less than approximately 0.5, and thus correction may be avoided. Avoidance of a correction when $\alpha$ is less than approximately 0.5 may eliminate unnecessary computation and save time.

Figure 5:
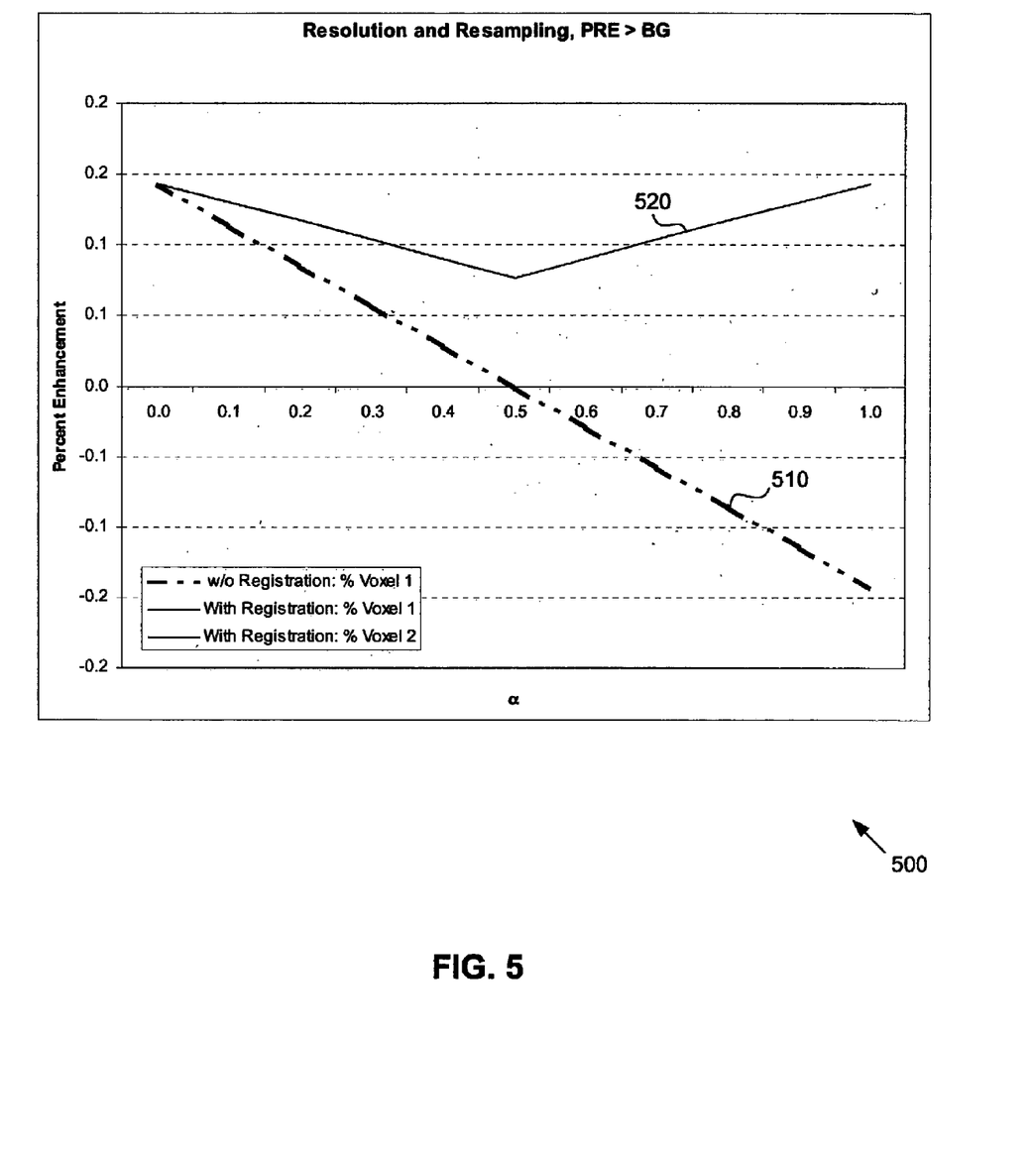
FIG. 5 is a graph relating a fractional normalized tissue displacement to an uncorrected and a corrected postcontrast signal enhancement percentage when precontrast imaging signals are greater than or generally greater than background imaging signals.

FIG. 5 is a graph 500 relating a fractional normalized tissue displacement $\alpha$ to an uncorrected postcontrast signal enhancement percentage curve or line 510 and a corrected postcontrast signal enhancement percentage curve or line 520 when precontrast imaging signals are greater than or generally greater than background imaging signals. As discussed above with respect to FIGS. 3-4, the curve 520 comprises two curve portions showing the percent enhancement from voxel 1 and voxel 2, respectively, with the curve 520 showing only the maximum percent enhancement. In FIG. 5, the values of BG, PRE, and POST are respectively defined as 100, 150, and 200. As shown in FIG. 5, the corrected curve 520 enhances, increases, or maximizes imaging accuracy relative to the uncorrected curve 510 under such circumstances. Thus, in one embodiment, the present invention may perform a correction when PRE is greater than BG independent of a value of $\alpha$; or possibly determine a different type of resampling procedure that may give rise to a transition value or transition region for a when PRE is greater than BG, and selectively initiate or perform a correction in accordance therewith.

The foregoing examples considered an effect of patient motion relative to resolution along a single axis or dimension. Certain embodiments may consider patient or tissue motion along an axis that corresponds to a lowest image resolution. In MRI situations, an axis of lowest resolution typically corresponds to image slice thickness, and is commonly defined as a z axis. In general, various embodiments of systems and/or methods in accordance with the present invention may adaptively consider resolution normalized fractional shifts (i.e., $\alpha$) and/or mathematical equivalents thereto and/or analogs thereof along or in multiple dimensions, including a dimension of lowest resolution. Depending upon embodiment details, systems and methods in accordance with the present invention that consider an $\alpha_x$, an $\alpha_y$, and/or an $\alpha_z$ and/or one or more mathematical equivalents thereto and/or analogs thereof may adaptively select between performing no correction, a two dimensional (2D) correction, and/or a three dimensional (3D) correction.

Figure 6:
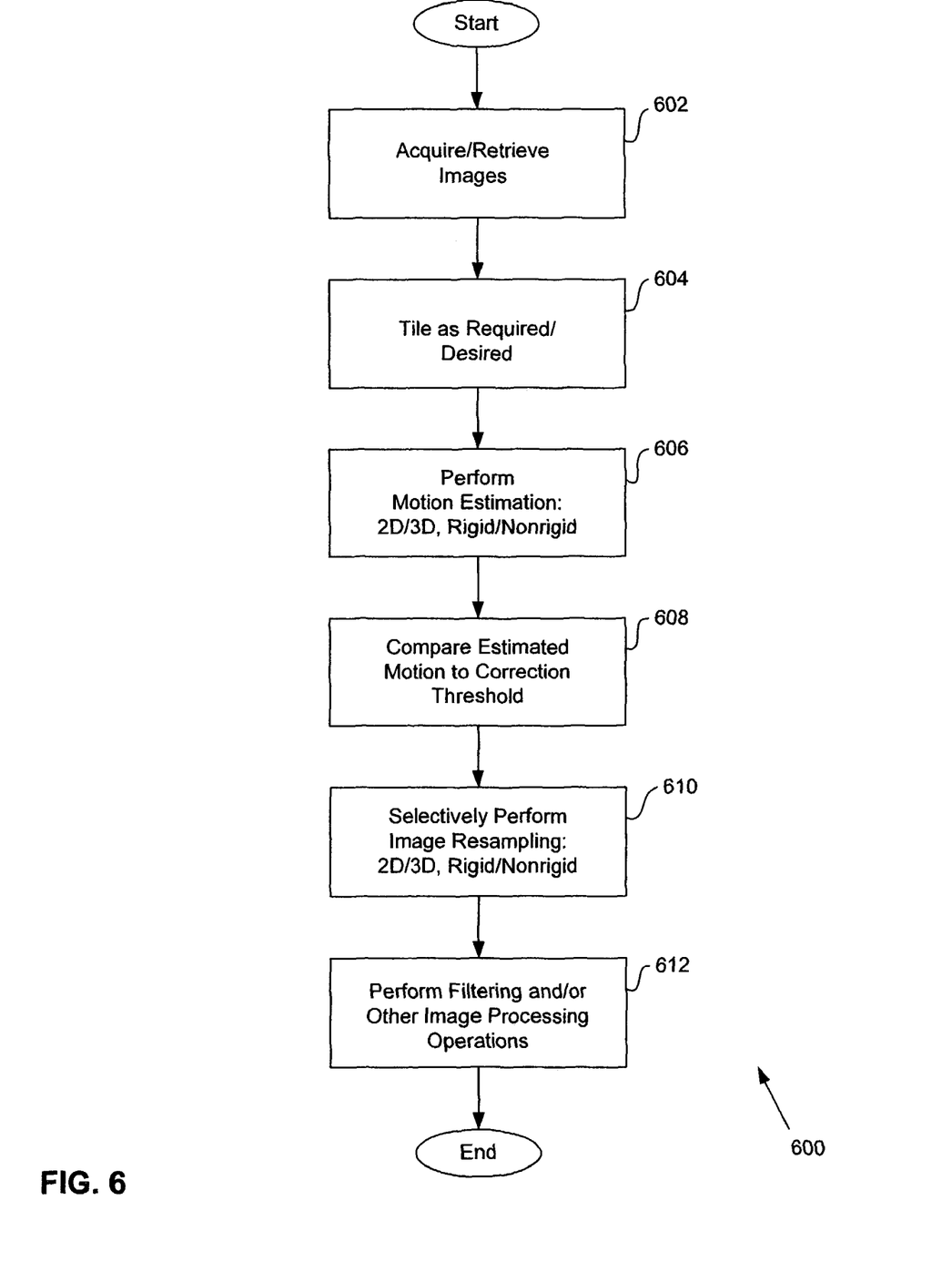
FIG. 6 is a flowchart of a procedure for adaptive registration of medical images according to an embodiment of the invention.

FIG. 6 is a flowchart of a procedure 600 for adaptive registration of medical images according to an embodiment of the invention. In one embodiment, the adaptive registration procedure 600 includes an acquisition procedure 602 that involves acquiring, generating, retrieving, receiving, and/or obtaining imaging data corresponding to a set or series of medical images. In one embodiment, the acquisition procedure 602 involves or is directed toward precontrast and/or postcontrast image slices, which may correspond to breast images or other types of MR images.

The adaptive registration procedure 600 may further include a tiling procedure 604 involving determination of whether registration should consider a local subset of imaging data or global imaging data; and identification or specification of one or more local subset parameters if applicable. Relative to breast MRI, a tiling procedure 604 may determine whether to perform registration in accordance with a window or subset of imaging information associated with a plurality of image slices. For example, a tiling procedure 604 may determine that registration corresponding to precontrast and/or postcontrast imaging data for a left breast is appropriate or required, and ignore imaging data for a right breast. Depending upon embodiment details, one or more portions of a tiling procedure 604 may involve manual input and/or an automated procedure.

The adaptive registration procedure 600 may additionally include a motion estimation procedure 606, which involves estimating, approximating, or determining patient or tissue motion based upon the imaging data under consideration. Motion estimation may involve generating one or more motion vectors by determining and/or optimizing a set of spatial transform parameters defined in accordance with a motion model. The motion model may be capable of accounting for various types of 2D or 3D motion or deformation of rigid and/or nonrigid tissues.

In general, a number of motion estimation techniques suitable for medical imaging and/or image processing may be applicable to various embodiments of the present invention. Descriptions of such motion estimation techniques may be found in references such as (a) "Comparison and Evaluation of Retrospective Intermodality Brain Image Registration Techniques," West et al., *JCAT* 1997; and (b) "A Survey of Medical Image Registration," Maintz and Viergever, *Medical Image Analysis*, 1998.

In one embodiment, the motion estimation procedure 606 may involve selection or identification of a motion model and/or a motion estimation technique; selection or identification of a reference image; and/or determination of one or more motion vectors or parameters for a set of images relative to the reference image along an axis or direction of lowest resolution (typically the axis corresponding to slice thickness in MRI situations) as well as one or more other axes. Selection of a motion model and/or a motion estimation technique may involve manual input and/or one or more automated procedures, possibly based upon clinical conditions such as imaging technology type and configuration, tissue types under consideration, image resolution, and/or other factors. In general, motion estimation in accordance with a nonrigid motion model is more computationally intensive than motion estimation in accordance with a rigid motion model, and 3D motion estimation is more computationally intensive than 2D motion estimation. Thus, selection or identification of a motion model and/or a motion estimation technique may additionally or alternatively be based upon available computational resources or capabilities. An alternate embodiment may rely upon a single type of motion model and/or motion estimation technique.

In accordance with the motion estimation procedure 606, determination of one or more motion vectors and/or motion parameters may involve operations in a spatial (voxel) domain or a spectral (frequency) domain. In one embodiment, a motion estimation procedure 606 may involve a minimization of gray level or voxel property based similarity measures in accordance with an optimization procedure (for example, a simplex minimization, a direction set, a conjugate gradient, or a simulated annealing procedure). Gray level similarity measures may include a sum of squared or absolute differences; a cross-correlation measure; an intensity ratio variance; mutual information; and/or a deterministic or stochastic sign change. A sum of squared differences technique may be computationally efficient at the possible expense of some accuracy, while a mutual information technique may be highly accurate at the possible expense of some computational speed. In an embodiment that performs motion estimation in accordance with an affine transform, a least squares technique rather than an optimization search may provide a direct solution.

During the motion estimation procedure 606, images or imaging data under consideration may be scaled or reduced in size to generate an initial motion estimate; and then scaled or increased to an original size to generate a final motion estimate, which may provide increased robustness. For example, a motion estimation procedure 604 directed toward images characterized by a 512×512 resolution may first estimate motion at a 64×64 resolution, then estimate motion at a 128×128 resolution, subsequently estimate motion at a 256×256 resolution, and finally estimate motion at a 512×512 resolution. Images or imaging data under consideration may additionally or alternatively be subdivided into smaller blocks for local motion estimation, which may be useful for estimating nonrigid motion.

The adaptive registration procedure 600 may further include an evaluation procedure 608 that involves comparing a result generated or obtained by the motion estimation procedure 606 to a correction threshold. In one embodiment, a motion estimation result may comprise a motion vector that may specify or indicate an estimated motion value along one or more axes, including an axis corresponding to lowest image resolution. As indicated above, for MRI image data, the axis of lowest resolution is typically an axis corresponding to image slice thickness, and is commonly defined as z. In one embodiment, a correction threshold may comprise a resolution value corresponding to one or more axes, including a lowest resolution axis, where each such resolution value is multiplied by a corresponding fraction. Thus, a correction threshold may specify or correspond to a fractional resolution along one or more axes.

The evaluation procedure 608 may determine whether one or more motion estimation results are greater or less than corresponding correction thresholds. Alternatively or additionally, the evaluation procedure 608 may determine whether one or more motion estimation results fall within particular corresponding correction ranges. Evaluation or comparison of a motion estimation result relative to a fractional resolution value may be mathematically equivalent or analogous to determining an $\alpha$ value of a type described above. The value of a correction threshold may be influenced by imaging technology; actual and/or expected background, precontrast, and/or postcontrast signal intensities; and/or other factors. One or more correction thresholds may be stored in and/or retrieved from a memory such as a lookup table based upon applicability to particular clinical situations.

The adaptive registration procedure 600 may further include a selective correction procedure 610 that involves selectively initiating or performing an image resampling or correction in accordance with a 2D or 3D rigid or nonrigid correction based upon a result obtained by or in conjunction with an evaluation procedure 608. Depending upon implementation details, the selective correction procedure 610 may additionally involve selectively avoiding image resampling or correction. Exemplary evaluation 608 and adaptive registration 600 procedures are further described below. Following the selective correction procedure 610, the adaptive registration procedure 600 may also include an adjustment procedure 612 that involves performing filtering and/or other image processing operations. These adjustment procedures may include, by way of example, noise reduction, contrast enhancement, and window and level procedures. Such adjustment procedures are well known in the art and need not be described herein.

Figure 7:
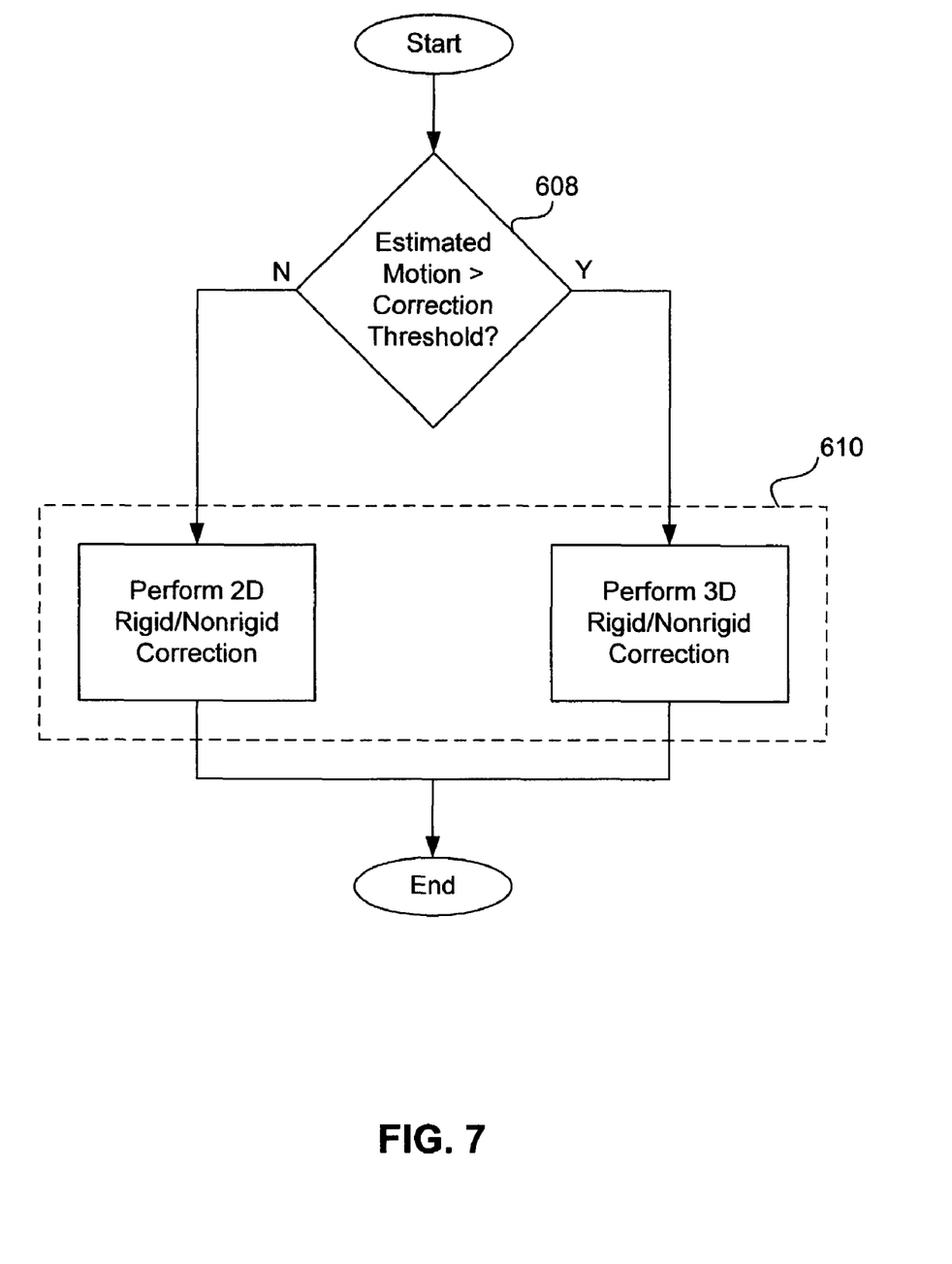
FIG. 7 is a flowchart of exemplary evaluation and selective correction procedures according to an embodiment of the invention.

FIG. 7 is a flowchart of exemplary evaluation 608 and selective correction 610 procedures according to an embodiment of the invention. Relative to FIG. 6, like reference numbers indicate like procedures, and the z axis corresponds to a lowest resolution dimension. In one embodiment, the evaluation procedure 608 determines whether estimated motion along the z axis equals, approximately equals, or exceeds a correction threshold, for example, 0.5 times z axis resolution. Thus, if resolution along z equals 1.5 mm, the evaluation procedure 608 may determine whether estimated motion along z exceeds 0.75 mm (corresponding to a situation in which $\alpha$ equals 0.5). If so, the selective correction procedure 610 may initiate and/or perform a 3D rigid or nonrigid correction; otherwise, the selective correction procedure 610 may initiate and/or perform a 2D rigid or nonrigid correction. A 3D correction may provide greater accuracy than a 2D correction, but will generally require significantly more computational time than a 2D correction. Thus, unless patient or tissue movement is significant relative to resolution, a 3D correction may be unnecessary, and particular embodiments of the invention may save time by performing a 2D correction. Performance of a rigid or nonrigid correction may be dependent upon a type of motion model and/or motion estimation technique employed during the motion estimation procedure 606, clinical conditions, tissue types under consideration, available computational resources, and/or computation time goals or constraints.

Figure 8:
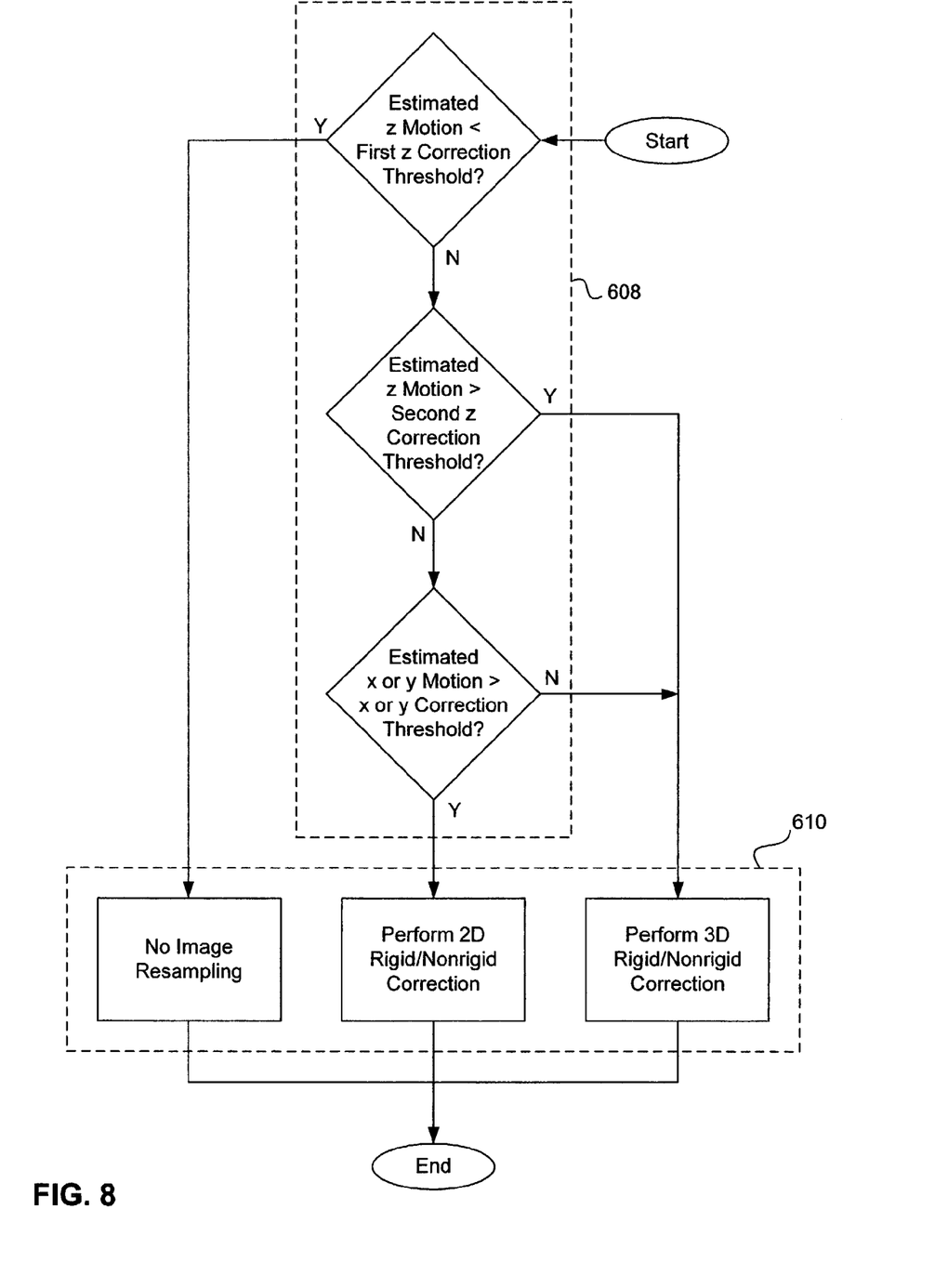
FIG. 8 is a flowchart of exemplary evaluation and selective correction procedures according to another embodiment of the invention.

FIG. 8 is a flowchart of exemplary evaluation 608 and selective correction 610 procedures according to another embodiment of the invention. Relative to FIG. 6, like reference numbers indicate like procedures, and the z axis corresponds to a lowest resolution dimension. In one embodiment, the evaluation procedure 608 may determine whether estimated motion along the z axis is less than a first z axis correction threshold, for example, 0.1 times z axis resolution. If so, image resampling or correction is avoided. Otherwise, the evaluation procedure 608 may determine whether estimated motion along the z axis equals, approximately equals, or exceeds a second z axis correction threshold, for example, 0.5 times z axis resolution. If so, the selective correction procedure 610 may initiate and/or perform a 3D rigid or nonrigid correction. Otherwise, the evaluation procedure 608 may determine whether estimated motion along an x or y axis equals, approximately equals, or exceeds a corresponding x axis or y axis correction threshold. In one embodiment, an x or y axis correction threshold may be, for example, 0.8 times x or y resolution, respectively. If estimated motion along an x or y axis meets the aforementioned conditions, the selective correction procedure 610 may initiate and/or perform a 3D rigid or nonrigid correction. Otherwise, the selective correction procedure 610 may initiate or perform a 2D rigid or nonrigid correction. Performance of a rigid or nonrigid correction may be dependent upon a type of motion model and/or motion estimation technique employed, and/or computational resources.

Figure 9:
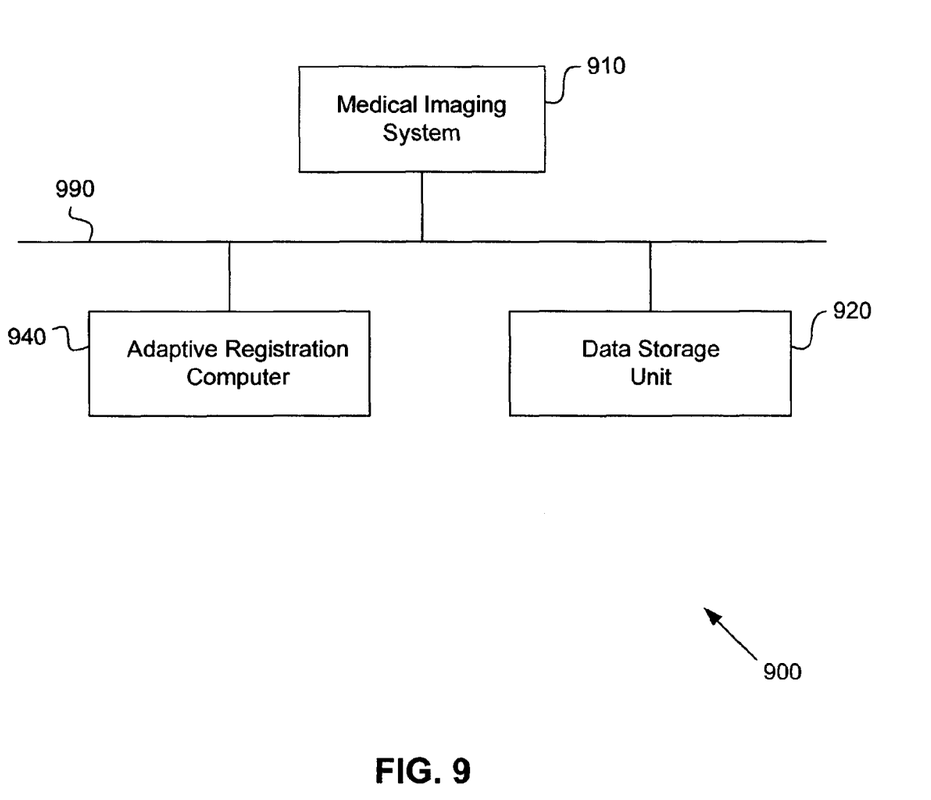
FIG. 9 is a block diagram of a system for adaptive registration of medical images according to an embodiment of the invention.

FIG. 9 is a block diagram of a system 900 for adaptive medical image registration according to an embodiment of the invention. The system 900 may comprise a medical imaging system 910, at least one data storage unit 920, and an adaptive registration computer 940. In one embodiment, each element 910, 920, 940 is coupled to a computer network 990.

The medical imaging system 910 may comprise an MRI or other type of imaging system. The data storage unit 920 may comprise one or more hard disk drives, and may possibly comprise a Network Attached Storage (NAS) device. The data storage unit 920 may receive, store, and/or transfer imaging data as well as other information.

The adaptive registration computer 940 may comprise one or more portions of a medical image analysis platform. The adaptive registration computer 940 may include a processing unit and a memory, and may further include one or more of a disk drive and/or other data storage devices (e.g., optical and/or magnetooptical data storage devices, tape drives, flash memory based drives, etc.), an input device, and an output device. The memory, the disk drive, and/or other data storage devices may comprise one or more portions of computer readable media that store program instructions and possibly data for performing one or more adaptive medical image registration procedures and/or operations associated therewith in accordance with particular embodiments of the invention. Depending upon implementation details, the network 990 may comprise one or more local or private networks such as a Local Area Network (LAN) and/or one or more public networks such as the Internet. In an alternate embodiment, the medical imaging system 910 and the adaptive registration computer 940 may each have a separate data storage unit 920, and imaging data and/or other information stored upon removable media may be manually transferred between such data storage units 920.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method for adaptive registration of a set of three dimensional medical images corresponding to first and second acquisitions of a particular patient by a single imaging modality, wherein a first acquisition image and a second acquisition image differ in one of background signal intensity and signal intensity of analogous structures, comprising:
   obtaining medical image data produced by a single medical imaging modality at first and second acquisition times;
   prior to any resampling, estimating an amount of patient motion that occurred between first and second acquisitions of the data by the medical imaging modality;
   selectively performing one of a two dimensional image resampling, a three dimensional image resampling, and no image resampling based on the estimated amount of patient motion; and generating a medical image representative of internal anatomical features of the patient.

2. The method of claim 1, wherein estimating the amount of patient motion comprises performing a motion estimation procedure that involves patient motion in a directional axis corresponding to a lowest image resolution.

3. The method of claim 2, wherein the axis corresponds to an MRI slice thickness.

4. The method of claim 1, wherein estimating the amount of patient motion comprises performing one estimated motion procedure selected from the group of a two dimensional and a three dimensional motion estimation procedure in accordance with one motion model selected from the group of a rigid and a non-rigid motion model.

5. The method of claim 1, wherein selectively performing an image resampling comprises:
   performing a comparison between the estimated amount of patient motion and a correction threshold; and
   performing the image resampling based upon the comparison.

6. The method of claim 5, wherein the correction threshold corresponds to a fraction of an image resolution.

7. The method of claim 6, wherein the fraction has a value approximately between 0.4 and 0.8.

8. The method of claim 6, wherein the fraction has a value of approximately 0.5.

9. The method of claim 5, wherein the correction threshold corresponds to a fraction of an image resolution along a lowest image resolution axis.

10. The method of claim 9, wherein the axis corresponds to an MRI image slice thickness.

11. The method of claim 6, wherein the set of medical images comprises a set of imaging signals, wherein an imaging signal may be characterized relative to a background imaging signal intensity, a precontrast imaging signal intensity corresponding to a lesion, and a postcontrast imaging signal intensity corresponding to the lesion, and wherein the fraction has a value that depends upon at least one from the group of a background imaging signal intensity, a precontrast imaging signal intensity, and a postcontrast imaging signal intensity.

12. The method of claim 5, wherein performing the image resampling comprises performing a first image resampling procedure in the event that the estimated amount of patient motion equals or exceeds the correction threshold and performing a second image resampling procedure in the event that the estimated amount of patient motion is less than the correction threshold.

13. The method of claim 5, wherein performing the image resampling comprises performing a three dimensional image resampling procedure in the event that the estimated amount of patient motion equals or exceeds the correction threshold.

14. The method of claim 5, wherein performing the image resampling comprises performing a two dimensional image resampling procedure in the event that the estimated amount of patient motion is less than the correction threshold.

15. A method for adaptive registration of a set of three dimensional medical images corresponding to first and second acquisitions of a particular patient by a single imaging modality, wherein a first acquisition image and a second acquisition image differ in one of background signal intensity and signal intensity of analogous structures, comprising:
   obtaining medical image data produced by a single medical imaging modality at first and second acquisition times;
   prior to any resampling, estimating an amount of patient motion that occurred between first and second acquisitions of the image data by the medical imaging modality; and
   performing a comparison between the estimated amount of patient motion and a correction threshold;
   performing a three dimensional image resampling procedure in the event that the estimated amount of patient motion equals or exceeds the correction threshold; and
   performing a two dimensional image resampling procedure in the event that the estimated amount of patient motion is less than the correction threshold; and generating a medical image representative of internal anatomical features of the patient.

16. The method of claim 15, wherein the correction threshold corresponds to a fraction of an image resolution.

17. The method of claim 16, wherein the fraction has a value between approximately 0.4 and 0.8.

18. The method of claim 16, wherein the fraction has a value of approximately 0.5.

19. The method of claim 15, wherein the correction threshold corresponds to a fraction of an image resolution along a lowest image resolution axis.

20. The method of claim 19, wherein the axis corresponds to an MRI image slice thickness.

21. The method of claim 15, further comprising the step of avoiding an image resampling in the event that the estimated amount of patient motion is less than the correction threshold by a predetermined amount.

22. A method for adaptive registration of a set of three dimensional medical images corresponding to first and second acquisitions of a particular patient by a single imaging modality, wherein a first acquisition image and a second acquisition image differ in one of background signal intensity and signal intensity of analogous structures, comprising:
    obtaining medical image data produced by a single medical imaging modality at first and second acquisition times;
    prior to any resampling, estimating an amount of patient motion that occurred between first and second acquisitions of the image data by the medical imaging modality; and
    prior to any resampling, performing a comparison between the estimated amount of patient motion and a first correction threshold;
    performing one of a two dimensional, three dimensional, rigid, and nonrigid image resampling procedure in the event that the estimated amount of patient motion equals or exceeds the first correction threshold; and
    avoiding an image resampling in the event that the estimated amount of patient motion is less than the first correction threshold; and generating a medical image representative of internal anatomical features of the patient.

23. The method of claim 22, wherein the correction threshold corresponds to a fraction of an image resolution.

24. The method of claim 23, wherein the fraction has a value between approximately 0.4 and 0.8.

25. The method of claim 23, wherein the fraction has a value of approximately 0.5.

26. The method of claim 22, wherein the correction threshold corresponds to a fraction of an image resolution along a lowest image resolution axis.

27. The method of claim 26, wherein the axis corresponds to an MRI image slice thickness.

28. The method of claim 23, wherein the set of medical images comprises a set of imaging signals, wherein an imaging signal may be characterized relative to a background imaging signal intensity, a precontrast imaging signal intensity corresponding to the lesion, and a postcontrast imaging signal intensity corresponding to a lesion, and wherein the fraction has a value that depends upon at least one from the group of a background imaging signal intensity, a precontrast imaging signal intensity, and a post contrast imaging signal intensity.

29. A system for adaptive registration of a set of three dimensional medical images generated by a single medical imaging modality and representative of internal anatomical features of a particular patient at first and second acquisition times, wherein a first acquisition image and a second acquisition image differ in one of background signal intensity and signal intensity of analogous structures, comprising:
    a processing unit; and
    a computer readable medium containing program instructions to cause the processing unit to:
        prior to any resampling, estimate an amount of patient motion that occurred between first and second acquisitions of the image data by the medical imaging modality;
        perform a comparison between the estimated amount of patient motion and a correction threshold; and
        select one from the group of performing a two dimensional image resampling procedure, performing a three dimensional image resampling procedure, and avoiding an image resampling in accordance with a relationship between the estimated amount of patient motion and the correction threshold.

30. The system of claim 29, wherein the correction threshold corresponds to a fraction of an image resolution.

31. The system of claim 30, wherein the fraction has a value between approximately 0.4 and 0.8.

32. The system of claim 30, wherein the fraction has a value of approximately 0.5.

33. The system of claim 29, wherein the correction threshold corresponds to a fraction of an image resolution along a lowest image resolution.

34. The system of claim 33, wherein the axis corresponds to an MRI image slice thickness.

35. The system of claim 29, wherein performing the first image resampling procedure comprises performing a three dimensional image resampling in the event that the estimated amount of patient motion equals or exceeds the correction threshold.

36. The system of claim 29, wherein performing the second image resampling procedure comprises performing a two dimensional image resampling in the event that the estimated amount of patient motion is less than the correction threshold.

37. The system of claim 29, wherein avoiding an image resampling comprises avoiding an image resampling in the event that the estimated amount of patient motion is less than the correction threshold by a predetermined amount.

38. The system of claim 29, wherein the medical imaging system comprises an MRI system.

39. The system of claim 38, wherein the medical imaging system comprises a breast MRI system and the processing unit processes breast medical image data.

40. A non-transitory computer readable medium storing program instructions to cause a processor to:
    obtain three dimensional medical image data produced by a single medical imaging modality of a particular patient at first and second acquisition times, wherein a first acquisition image and a second acquisition image differ in one of background signal intensity and signal intensity of analogous structures;
    prior to any resampling procedure, estimate an amount of patient motion that occurred between first and second acquisitions of the image data by the medical imaging modality; and
    select one from the group of performing a two dimensional image resampling procedure, performing a three dimensional image resampling procedure, performing a rigid image resampling procedure, performing a nonrigid resampling procedure, and avoiding an image resampling in accordance with a relationship between the estimated amount of patient motion and a correction threshold to thereby generate a medical image representative of internal anatomical features of the patient.

41. The computer readable medium of claim 40, wherein the correction threshold comprises a fraction of an image resolution.

42. The computer readable medium of claim 41, wherein the fraction has a value between approximately 0.4 and 0.8.

43. The computer readable medium of claim 41, wherein the fraction has a value of approximately 0.5.

44. The computer readable medium of claim 40, wherein the correction threshold corresponds to a fraction of an image resolution along a lowest image resolution axis.

45. The computer readable medium of claim 44, wherein the axis corresponds to an MRI image slice thickness.

46. The computer readable medium of claim 40, wherein the three dimensional image resampling is performed in the event that the estimated amount of patient motion equals or exceeds the correction threshold.

47. The computer readable medium of claim 40, wherein the two dimensional image resampling is performed in the event that the estimated amount of patient motion is less than the correction threshold.

48. The computer readable medium of claim 40, wherein avoiding the image resampling comprises avoiding the image resampling in the event that the estimated amount of patient motion is significantly less than the correction threshold by a predetermined amount.

49. The computer readable medium of claim 22, wherein the two-dimensional resampling is performed if the estimated amount of patient motion is less than a second correction threshold and the three-dimensional resampling is performed if the estimated amount of patient motion exceeds a second correction threshold.

50. The method of claim 2, wherein the axis corresponds to a CT slice thickness.

* * * * *